United States Patent
Chavali et al.

(10) Patent No.: US 11,627,710 B2
(45) Date of Patent: *Apr. 18, 2023

(54) METHODS AND SYSTEMS FOR IDENTIFYING HYBRIDS FOR USE IN PLANT BREEDING

(71) Applicant: Monsanto Technology LLC, St. Louis, MO (US)

(72) Inventors: Srinivas Phani Kumar Chavali, St. Louis, MO (US); Sambarta Dasgupta, St. Louis, MO (US); Mahdi Jadaliha, Chesterfield, MO (US); Nalini Polavarapu, St. Louis, MO (US); Zi Wang, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1051 days.

This patent is subject to a terminal disclaimer.

(21) Appl. No.: 16/213,677

(22) Filed: Dec. 7, 2018

(65) Prior Publication Data

US 2019/0174691 A1  Jun. 13, 2019

Related U.S. Application Data

(60) Provisional application No. 62/596,907, filed on Dec. 10, 2017.

(51) Int. Cl.
| | | |
|---|---|---|
| *A01H 1/04* | (2006.01) | |
| *C12Q 1/6827* | (2018.01) | |
| *C12Q 1/6895* | (2018.01) | |
| *G16B 5/00* | (2019.01) | |
| *G16B 20/00* | (2019.01) | |
| *G16B 40/00* | (2019.01) | |
| *G16B 50/00* | (2019.01) | |
| *G16B 40/30* | (2019.01) | |
| *G16B 40/20* | (2019.01) | |

(52) U.S. Cl.
CPC .............. *A01H 1/04* (2013.01); *C12Q 1/6827* (2013.01); *C12Q 1/6895* (2013.01); *G16B 5/00* (2019.02); *G16B 20/00* (2019.02); *G16B 40/00* (2019.02); *G16B 40/20* (2019.02); *G16B 40/30* (2019.02); *G16B 50/00* (2019.02); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 6,285,999 B1 | 9/2001 | Page |
| 7,269,587 B1 | 9/2007 | Page |
| 9,727,639 B2 | 8/2017 | Groeneveld et al. |
| 9,727,926 B2 | 8/2017 | Napper et al. |
| 9,734,239 B2 | 8/2017 | Allen et al. |
| 10,327,400 B2 | 6/2019 | Chavali et al. |
| 2005/0144664 A1 | 6/2005 | Smith et al. |
| 2007/0083456 A1 | 4/2007 | Akers |
| 2010/0100980 A1 | 4/2010 | Bull et al. |
| 2011/0224911 A1 | 9/2011 | Ostrander et al. |
| 2013/0117878 A1 | 5/2013 | Bink et al. |
| 2013/0340110 A1 | 12/2013 | Robbins et al. |
| 2014/0130200 A1 | 5/2014 | Bliss |
| 2015/0080238 A1 | 3/2015 | Ragot et al. |
| 2017/0156276 A1 | 6/2017 | Bull et al. |
| 2017/0223947 A1 | 8/2017 | Gall et al. |
| 2017/0295735 A1 | 10/2017 | Butruille et al. |
| 2017/0354105 A1 | 12/2017 | Polavarapu et al. |
| 2019/0180845 A1 | 6/2019 | Chavali et al. |
| 2019/0313591 A1 | 10/2019 | Chavali et al. |

FOREIGN PATENT DOCUMENTS

| | | |
|---|---|---|
| CN | 1895028 | 1/2007 |
| CN | 101410008 | 4/2009 |
| CN | 101583956 A | 11/2009 |
| CN | 102334123 | 1/2012 |
| WO | WO2008/087185 A1 | 7/2008 |
| WO | WO 2013/026085 A1 | 2/2013 |
| WO | WO 2016/022517 A1 | 2/2016 |

(Continued)

OTHER PUBLICATIONS

Faux, Anne-Michelle et al., "AlphaSim: Software for Breeding Program Simulation", The Plant Genome, vol. 9, No. 3, Nov. 2016 (published Sep. 22, 2016), pp. 1-14.

Lado, Bettina et al., "Strategies for Selecting Crosses Using Genomic Prediction in Two Wheat Breeding Programs", The Plant Genome, vol. 10, No. 2, Jul. 2017 (published Jul. 13, 2017), pp. 1-13.

Charcosset, A. et al., "Prediction of Maize Hybrid Silage Performance Using Marker Data: Comparison of Several Models for Specific Combining Ability", Crop Science, vol. 38, No. 1, Jan. 1998, pp. 38-44.

Xu, S. et al., "Predicting hybrid performance in rice using genomic best linear unbiased prediction", Proceedings of the National Academy of Sciences, vol. 111, No. 34, Aug. 2014, pp. 12456-12461.

(Continued)

*Primary Examiner* — G Steven Vanni

(74) *Attorney, Agent, or Firm* — Harness, Dickey & Pierce, P.L.C.

(57) ABSTRACT

Exemplary methods for identifying hybrids for use in a plant breeding pipeline are disclosed. One exemplary computer-implemented method includes accessing a data structure including data representative of a pool of hybrids and determining a prediction score for at least a portion of the hybrids included in the pool based on the data included in the data structure. The prediction score is indicative of a probability of selection and/or a probability of success of the hybrid based on historical data. The method further includes selecting a group of hybrids from the pool based on the prediction score, identifying a set of hybrids, from the group of hybrids, based on an expected performance of the set of hybrids and/or one or more factors associated with the hybrids and/or lines making up the hybrids, and also directing the set of hybrids to a further iteration or different phase in the breeding pipeline.

6 Claims, 4 Drawing Sheets

(56) References Cited

FOREIGN PATENT DOCUMENTS

WO    WO 2016/025848 A1    2/2016
WO    WO 2017/214445 A1    12/2017

OTHER PUBLICATIONS

Akdemir, Deniz, and Julio I. Sánchez. "Efficient brewing by genomic mating." *Frontiers in genetics* 7 (2016), 11 pages.
Bishop, Christopher M., Pattern recognition and machine learning, Springer (2006) 758 pages.
Bellobás, Béla, Graduate Texts in Mathematics, *Modem graph theory*. vol. 184. Springer Science & Business Media, 2013, 409 pages.
Ensemble Methods in Data Mining: Improving Accuracy Through Combining Predictions, Giovanni Seni and John Elder, 2010 (Morgan and Claypool Publishers), 126 pages.
Ensemble-based classifiers, Rokach (2010), *Artificial Intelligence Review* 33 (1-2): 1-39.
Fernández-Madrigal, J-A., and Javier González. "Multihierarchical graph search." *IEEE Transactions on Pattern Analysis and Machine Intelligence* 24.1 (2002): 103-113.
Fortunato, Santo. "Community detection in graphs." *Physics reports* 486.3 (2010): 75-174.
Greg Linden, Brent Smith and Jeremy York. Amazon.com recommendations: Item-to-item collaborative filtering. IEEE Internet Computing, 7(1): 76-80, 2003.
Han, Ye, et al. "The Predicted Cross Value for Genetic Introgression of Multiple Alleles." *Genetics* 205.4 (2017): 1409-1423.
Isidro, Julio, et al. "Training Set optimization under population structure in genomic selection." *Theoretical and applied genetics* 128.1 (2015): 145-458.
Jure Leskovec, Lada A. Adamic, and Bernardo A. Huberman. The dynamics of viral marketing. ACM Transactions on the web (ACMTWEB), 1(1), 2007, 39 pages.
Lars Backstrom and Jure Leskovec. Supervised random walks: Predicting and recommending links in social networks. Proceeding of WSDM 2011, pp. 635-644, 2011.
Li, Xin, and Hsinchun Chen. "Recommendation as link prediction in bipartite graphs: A graph kernel-based machine learning approach." Decision Support Systems 54.2 (2013): 880-890.
Mirza, Batul J., Benjamin J. Keller, and Naren Ramakrishnan. "Studying recommendation algorithms by graph analysis." Journal of Intelligent Information Systems 20.2 (2003): 131-160.
Murphy, Kevin P., Machine learning: a probabilistic perspective (MIT press, 2012), 1105 pages.
Popular ensemble methods: An empirical study, Opitz & Maclin (1999), *Journal of Artificial Intelligence Research* 11: 169-98.
Stanford large network dataset collection. http://snap.stanford.edu/data/index.html, accessed Nov. 2017, 5 pages.
Thulasiraman, Krishnaiyan, and Madisetti NS Swamy. *Graphs: theory and algorithms*. John Wiley & Sons, 2011, 470 pages.
Wasserman, Stanley, and Katherine Faust. *Social network analysis: Methods and applications*. vol. 8. Cambridge university press (1994), 116 pages.
Zhou, Tao, et al. "Bipartite network projection and personal recommendation." Physical Review E 76.4 (2007): 046115.
Ivandro Bertan et al., Parental Selection Strategies in Plant Breeding Programs, Journal of Crop Science and Biotechnology, vol. 10, No. 4, Jan. 1, 2007, pp. 211-222.
Sun X et al., The role and basics of computer simulation in support of critical decisions in plant breeding, Molecular Breeding, Kluwer Academic Publishers, vol. 28, No. 4, Sep. 10, 2011, pp. 421-436.
Jannink et al., Genomic selection in plant breeding: from theory to practice, Briefings in Functional Genomics, vol. 9, No. 2, Feb. 15, 2010, pp. 166-177.

METHODS AND SYSTEMS FOR IDENTIFYING HYBRIDS FOR USE IN PLANT BREEDING

CROSS-REFERENCE TO RELATED APPLICATION

This application claims the benefit of and priority to U.S. Provisional Application No. 62/596,907, filed on Dec. 10, 2017. The entire disclosure of the above application is incorporated herein by reference.

FIELD

The present disclosure generally relates to systems and methods for use in plant breeding, and in particular, to systems and methods for identifying sets of hybrids, from pools of potential hybrids, and populating breeding pipelines with the identified sets of hybrids.

BACKGROUND

This section provides background information related to the present disclosure which is not necessarily prior art.

In plant development, modifications are made in the plants, either through selective breeding or genetic manipulation. And, when desirable improvements are achieved, commercial products are often developed through planting plants/seeds for the desirable improvements and harvesting resulting seeds over several generations. Throughout the development process, numerous decisions are made based on characteristics and/or traits of the plants being evaluated, and similarly on characteristics and/or traits of offspring, which are not guaranteed to inherit or exhibit the desired traits of parents. Traditionally, as part of selecting particular plants for further development, the genomes of the parents are evaluated for genetic sequences which, when crossed, may result in origins having the desired characteristics and/or traits, which may then be selected and/or filtered through testing of the plants. Plant development is known to involve large numbers of possible lines and origins from which final breeding decisions are made (and/or commercial products are selected) by breeders through conventional techniques.

DRAWINGS

The drawings described herein are for illustrative purposes only of selected embodiments, are not all possible implementations, and are not intended to limit the scope of the present disclosure.

Corresponding reference numerals indicate corresponding parts throughout the several views of the drawings.

DETAILED DESCRIPTION

Figure 1:
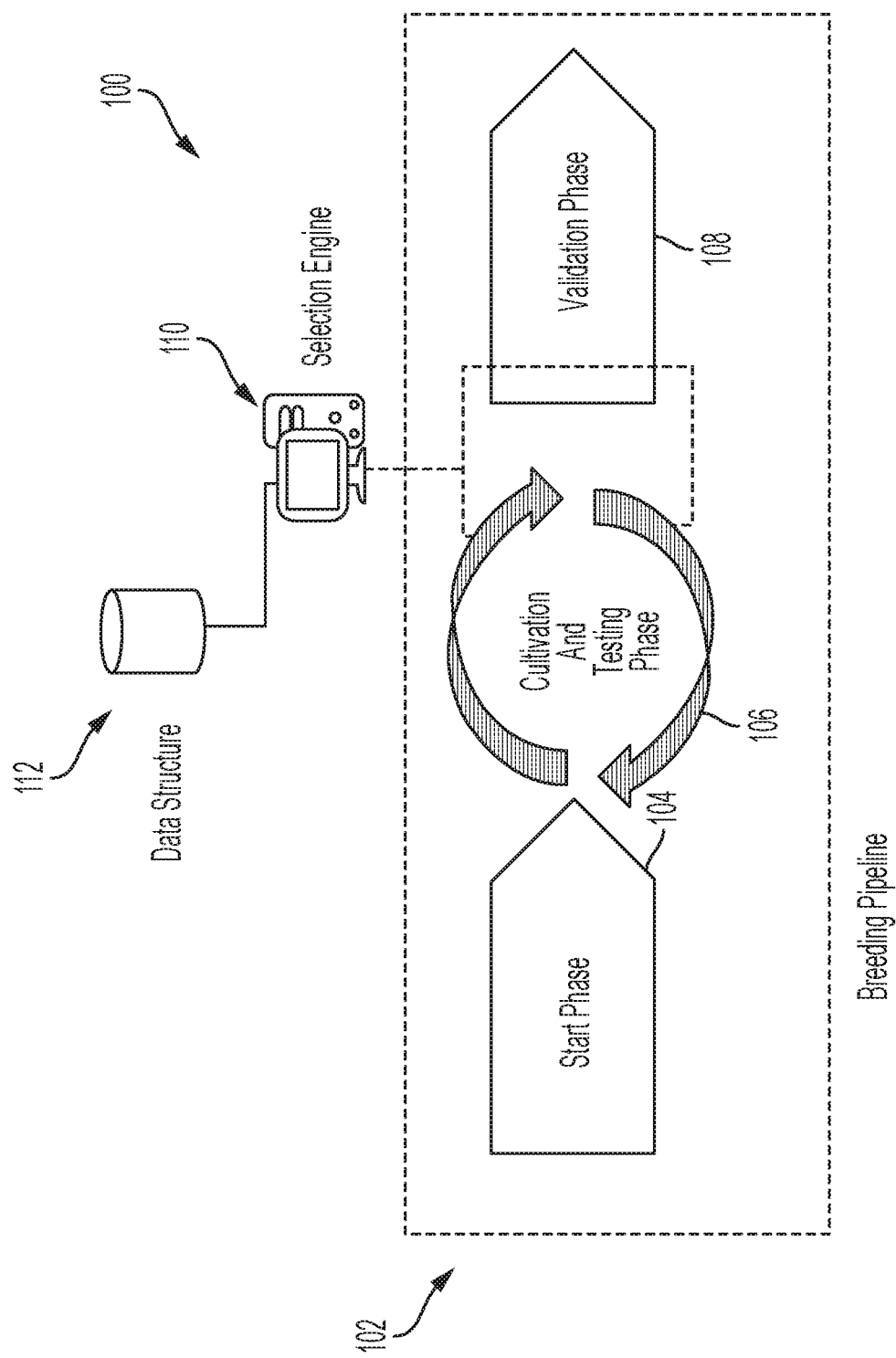
FIG. 1 illustrates an exemplary system of the present disclosure suitable for identifying a set of hybrids from a pool of potential hybrids for advancement in one or more breeding pipelines.

Exemplary embodiments will now be described more fully with reference to the accompanying drawings. The description and specific examples included herein are intended for purposes of illustration only and are not intended to limit the scope of the present disclosure.

Various breeding techniques are employed in agricultural industries to produce desired plants. An integral part of the process involves selecting lines with desirable trait(s) to cross with other lines having desirable trait(s) to generate hybrids having at least a portion of the desirable traits. However, it has been difficult to accurately select high performing hybrids given a number of lines and a pool of hybrids from which to select the hybrids, especially when the pool includes a substantial number of hybrids (e.g., in a commercial setting, etc.). For example, if a human breeder is given m number of male lines and n number of female lines, then, the pool of possible hybrids is N≤m×n, with a goal to select, for example, r number of hybrids for a breeding pipeline. As such, there are as many as $$C_r^{mn} = \frac{mn!}{(mn-r)!r!}$$

distinct sets of hybrids to be identified, which may be reduced $$\text{to} \sim \left(\frac{mn}{r}\right)^r.$$

In one illustrative example, where a human breeder is selecting one hundred hybrids (r) provided from one hundred male lines (m) and one hundred female lines (n), the number of potential sets to be identified, as an indicator of complexity, is quantified as about $10^{200}$. By this example, and other realistic numbers of lines/hybrids, it is clear that substantial complexity exists in selecting hybrids, especially when it is required and/or desired to account for trait distribution and/or genetic diversity.

Uniquely, the systems and methods herein permit identification of a set of hybrids from a pool of potential hybrids to be included in one or more breeding pipelines. In particular, a selection engine selects a group of hybrids, from the pool of hybrids, based on a prediction score, and then identifies the set of hybrids, from the group of hybrids, based on one or more further factors associated with the hybrids. Specifically, for example, as describe below, the selection engine may employ an algorithm that accounts for predicted performance, but controls the set of hybrids that are identified through one or more factors and/or restrictions (e.g., based on desired trait(s), line distributions, heterotic diversities, risks, or desired market segmentation, etc.). In this manner, complexities associated with the identification of the set of hybrids to be advanced toward commercialization may be mitigated and/or reduced, while maintaining substantial accuracy in the selection and accounting probable performance and/or and genetic diversity among the set of hybrids.

Hybrids are crosses of two individual plants or inbred lines, which are progenies of some historical origins. As used herein, lines refer to the parent(s) of a hybrid, and are interpreted as either singular or plural, as applicable. The lines may be split into genetically distinct groups, also known as heterotic groups. Heterotic groups may be referred to as "male pools" and "female pools." Male and female heterotic groups are identified as two sets, which are separable as two distinct groups, when marker based similarity, for example, is used as a measure of distance between inbred lines. Such terminology is utilized to distinguish the two heterotic groups from which two lines are selected for a given hybrid. The terms "male" and "female" are not intended to convey any information other than that the male and female lines are from different heterotic groups. Phenotypic data, trait distribution, ancestry, genetic sequence, commercial success, and additional information of a line are generally known and may be stored in memory, as described in more detail below.

As used herein, phenotypic data includes, but is not limited to, information regarding the phenotype of a given line or hybrid, or a population of the same. Phenotypic data may include the size and/or heartiness of the line (e.g., plant height, stalk girth, stalk strength, etc.), yield, time to maturity, resistance to biotic stress (e.g., disease or pest resistance), resistance to abiotic stress (e.g., drought or salinity resistance, etc.), growing climate, or any additional phenotypes, and/or combinations thereof. It should be appreciated that the systems and methods herein generally involve and/or rely on phenotypic data associated with one or more lines, hybrids, etc. That said, it should be appreciated that genotypic data may be used, in connection or in combination with the phenotypic data described herein (or otherwise) (e.g., to supplement the phenotypic data and/or to further inform the models, algorithms, and/or predictions herein, etc.), in one or more exemplary implementations, which may then aid in the selection of groups or sets of hybrids consistent with the description herein FIG. 1 illustrates an exemplary system 100 for identifying a set of hybrids from a pool of hybrids for advancement, in which one or more aspects of the present disclosure may be implemented. Although, in the described embodiment, parts of the system 100 are presented in one arrangement, other embodiments may include the same or different parts arranged otherwise depending, for example, on particular types of hybrids to be identified, etc.

As shown in FIG. 1, the system 100 generally includes a breeding pipeline 102, which is provided to identify a set of hybrids from a pool of hybrids to be advanced toward commercial product development. The breeding pipeline 102 generally defines a pyramidal progression; whereby it starts with a large number of hybrids (e.g., potential crosses of available lines, etc.), and successively narrows (e.g., reduces) the number of hybrids to preferred and/or desired hybrids. While the breeding pipeline 102 is configured to identify and/or select hybrids as provided herein, the breeding pipeline 102 may be configured to employ one or more other techniques which may include a wide range of methods known in the art, often depending on the particular plant and/or organism for which the breeding pipeline 102 is provided.

In certain breeding pipeline embodiments (e.g., large industrial breeding pipelines, etc.), testing, selections, and/or advancement may be directed to hundreds, thousands, or more lines, hybrids, etc., in multiple phases at several locations over several years to arrive at a reduced set of hybrids, etc., which are then selected for commercial product development. In short, the breeding pipeline 102 is configured, by the testing, selections, etc., included therein, to reduce a large number of lines and possible hybrids down to a relatively few number of hybrids which are predicted to perform as desired as commercial products.

In this exemplary embodiment, the breeding pipeline 102 is described with reference to, and is generally directed to, corn or maize and traits and/or characteristics thereof. However, it should be appreciated that the methods disclosed herein are not limited to corn and may be employed in a plant breeding pipeline/program relating to other plants, for example, to improve any fruits, vegetables, grasses, trees, or ornamental crops, including, but not limited to, maize (*Zea mays*), soybean (*Glycine max*), cotton (*Gossypium hirsutum*), peanut (*Arachis hypogaea*), barley (*Hordeum vulgare*); oats (*Avena sativa*); orchard grass (*Dactylis glomerata*); rice (*Oryza sativa*, including indica and *japonica* varieties); sorghum (*Sorghum bicolor*); sugar cane (*Saccharum* sp); tall fescue (*Festuca arundinacea*); turfgrass species (e.g., species: *Agrostis stolonifera, Poa pratensis, Stenotaphrum secundatum*, etc.); wheat (*Triticum aestivum*), and alfalfa (*Medicago sativa*), members of the genus *Brassica*, including broccoli, cabbage, cauliflower, canola, and rapeseed, carrot, Chinese cabbage, cucumber, dry bean, eggplant, fennel, garden beans, gourd, leek, lettuce, melon, okra, onion, pea, pepper, pumpkin, radish, spinach, squash, sweet corn, tomato, watermelon, honeydew melon, cantaloupe and other melons, banana, castorbean, coconut, coffee, cucumber, Poplar, Southern pine, *Radiata* pine, Douglas Fir, *Eucalyptus*, apple and other tree species, orange, grapefruit, lemon, lime and other citrus, clover, linseed, olive, palm, *Capsicum, Piper*, and Pimenta peppers, sugarbeet, sunflower, sweetgum, tea, tobacco, and other fruit, vegetable, tuber, and root crops. These methods herein may also be used in conjunction with non-crop species, especially those used as model systems, such as *Arabidopsis*. What's more, the systems and methods disclosed herein may be employed beyond plants, for example, for use in animal breeding programs, or other non-plant and/or non-crop breeding programs.

As shown in FIG. 1, the breeding pipeline 102 includes a hybrid start phase 104 and a cultivation and testing phase 106 (through one or more iterations), which together identify and/or select one or multiple hybrids for advancement on to a validation phase 108, in which the hybrids are introduced into pre-commercial testing, for example, depending on the particular type of hybrids or other suitable processes (e.g., a characterization and/or commercial development phase, etc.) with an intent and/or target to be planting and/or commercializing the hybrids. With that said, it should be appreciated that the breeding pipeline 102 may include a variety of conventional processes known to those skilled in the art in the three different phases 104, 106, and 108 illustrated in FIG. 1.

In the hybrid start phase 104, a pool of potential hybrids is provided from one or more sets of lines. The lines may be selected by a breeder, for example, or otherwise, depending on the particular type of plant, etc. The lines (and then origins associated therewith) may also be selected, for example, based on origin selection systems and/or based (at least in part) on the methods and systems disclosed in U.S. patent application Ser. No. 15/618,023, titled "Methods for Identifying Crosses for use in Plant Breeding," the entire disclosure of which is incorporated herein by reference. Once the lines, i.e., both male and female lines, are selected, the lines are combined to provide the pool of hybrids. The pool of hybrids is then directed to the cultivation and testing phase 106, in which the hybrids are planted or otherwise introduced into one or more growing spaces, such as, for example, greenhouses, shade houses, nurseries, breeding plots, fields, etc.

Once the hybrids are grown, each is tested to derive and/or collect phenotypic data for the hybrids, whereby the phenotypic data is stored in one or more data structures described below. Testing may include, for example, any suitable techniques for determining phenotypic data. Such techniques may include any number of tests, trials, or analyses known to be useful for evaluating plant performance, including any phenotyping known in the art. In preparation for such testing, samples of embryo and/or endosperm material/tissue may be harvested/removed from the progenies in a way that does not kill or otherwise prevent the seeds or plants from surviving the ordeal. For example, seed chipping may be employed to obtain tissue samples from the progenies for use in determining desired phenotypic data. Any other methods of harvesting samples of tissue can also be used, as conducting assays directly on the tissue of the seeds that do not require samples of tissue to be removed. In certain embodiments, the embryo and/or endosperm remain connected to other tissue of the seeds. In certain other embodiments, the embryo and/or endosperm are separated from other tissue of the seeds (e.g., embryo rescue, embryo excision, etc.). Common examples of phenotypes through such testing, include, without limitation, size, shape, surface area, volume, mass, and/or quantity of chemicals in at least one tissue of the seed, for example, anthocyanins, proteins, lipids, carbohydrates, etc., in the embryo, endosperm or other seed tissues. Where a hybrid (e.g., cultivated from a seed, etc.) has been selected or otherwise modified to produce a particular chemical (e.g., a pharmaceutical, a toxin, a fragrance, etc.), the hybrid can be assayed to quantify the desired chemical.

With that said, it should be appreciated that the cultivation and testing phase 106 of the breeding pipeline 102 in this embodiment is not limited to certain or particular testing techniques, as any techniques suitable to aid in the determination of relevant phenotypic data associated with the hybrids at any stage of the life cycle may be used. That said, in certain examples, it may be advantageous to use test techniques which may be conducted without germinating a seed of the hybrid and/or otherwise cultivating a plant sporophyte (e.g., via chipping of the seed as discussed above, etc.). It should further be appreciated that the cultivation and testing phase 106 of the breeding pipeline 102 may include multiple iterations, as indicated by the cycling arrows in FIG. 1, in which hybrids are grown and/or testing and selections are made, and whereby the pool of hybrids is reduced, with the hybrids being passed to a next iteration or to the validation phase 108. The testing performed within the cultivation and testing phase 106 may be adapted to include multiple iterations to provide the testing and/or data suitable to the hybrids and/or consistent the techniques described herein.

With continued reference to FIG. 1, transition of the hybrids from one cultivation and testing phase 106 to another (when cyclical) and/or a validation phase 108 is controlled, in the system 100, by a selection engine 110. The selection engine 110 includes a computing device, which may be a standalone computing service, or may be a computing device integrated with one or more other computing devices. The selection engine 110 facilitates control in identifying hybrids to transition within the cultivation and testing phase 106 from one iteration to the next (e.g., when multiple iterations are included, etc.), or to the validation phase 108 (as indicated by the dotted indicator), and more generally progression from one phase to the next.

The selection engine 110 is configured, by computer-executable instructions and/or one or more algorithms herein (or variants thereof), to perform the operations described herein. What's more, it should be appreciated that the selection engine 110 may be configured to provide (e.g., generate and cause to be displayed at a computing device of a human breeder) and/or respond to user interface(s), through which the human breeder (broadly, a user) is able to provide inputs regarding hybrids or desired traits for hybrids and/or usable by the algorithms herein (e.g., a number of hybrids selected, inputs indicative of market segments, inputs defining a desired trait profile, other inputs specific to one or more breeding strategies, or, more generally, other aspects of the identification of the set of hybrids; etc.). The user interface may be provided directly at a computing device (e.g., computing device 200 as described below, etc.) of the human breeder, in which the selection engine 110 is employed, or via one or more network-based applications through which a remote user (again, potentially the human breeder) may be able to interact with the selection engine 110 as described herein.

In addition, as shown in FIG. 1, the system 100 further includes a hybrid data structure 112 coupled to the selection engine 110. In this exemplary embodiment, the hybrid data structure 112 includes data related to lines and hybrids, etc. The data may include any type of data for the lines and hybrids, etc., which may be historical data (e.g., a last year, two, five, ten, fifteen, or more or less years of the plants through the cultivation and testing phases; etc.), and/or data related to a current iteration of the cultivation and testing phase 106, etc. The data may further be provided and/or generated in the breeding pipeline 102, or from outside the breeding pipeline 102.

Table 1 includes exemplary historical phenotypic data from a series of maize plant hybrids ($H_{1,1}$ through $H_{m,n}$), where variable values is provided for the yield and standability of each line from which the hybrid is derived. It should be appreciated that other data, and specifically, phenotypic data, may be included for both maize plants and other types of plants, as contemplated herein.

TABLE 1

| Hybrid | Female Line | Male Line | Yield F | Yield M | Stand F | Stand M | Historical Selection |
|---|---|---|---|---|---|---|---|
| $H_{1,1}$ | $F_1$ | $M_1$ | $Y_1$ | $Y_1$ | $S_1$ | $S_1$ | TRUE |
| $H_{1,2}$ | $F_1$ | $M_2$ | $Y_1$ | $Y_2$ | $S_1$ | $S_2$ | FALSE |
| ... | ... | ... | ... | ... | ... | ... | ... |
| $H_{m,n}$ | $F_n$ | $M_m$ | $Y_m$ | $Y_n$ | $S_n$ | $S_m$ | TRUE |

In addition to the specific phenotypic data for each hybrid, Table 1 of the hybrid data structure 112 further includes an advancement decision for the hybrid in one or more prior breeding cycles, year, and/or seasons in the breeding pipeline 102 or other breeding pipelines, etc. As shown, for example, the hybrids $H_{1,1}$ and $H_{m,n}$ were previously advanced ("TRUE"), while hybrid $H_{1,2}$ was not previously advanced ("FALSE").

In this exemplary embodiment, the selection engine 110 is configured to generate a prediction model, based on the historical data included in the hybrid data structure 112, in whole or in part, where the prediction model provides a probability of a hybrid being "advanced" for given phenotypic data. The selection engine 110 may employ any suitable technique to generate the prediction model (also referred to as a "prediction algorithm"). The techniques may include, without limitation, random forest, support vector machine, logistic regression, tree based algorithms, naïve Bayes, linear/logistic regression, deep learning, nearest neighbor methods, Gaussian process regression, and/or various forms of recommendation systems techniques, methods and/or algorithms to provide a manner of determining a probability of advance for a given set of data (e.g., yield, height, and standability for maize, etc.).

Specifically, for example, the prediction model may be consistent with random forest, which is an ensemble of multiple decision tree classifiers. Each of the decision trees are trained on a randomly sampled data from a training data set (e.g., such as included in Table 1, etc.). Further, a random subset of features (e.g., as indicated by the phenotypic data, etc.) may then be selected to generate the individual trees. The final prediction score, generated by the random forest, is computed, by the selection engine 110, as an aggregation of the individual trees and relevant to the prediction of TRUE or FALSE (i.e., advancement or not) relative to the features upon which the trees are generated.

Again, notwithstanding this specific example, it should be understood that any suitable technique may be employed, by the selection engine 110, to generate the prediction model.

Once the model is generated, the selection engine 110 is configured to determine a prediction score, based on the prediction model, for each of the hybrids in the pool of hybrids (in the present cultivation and testing phase 106). Specifically, when the hybrid from the pool of hybrids is tested, phenotypic data (e.g., yield, height, standability, oil content, pod counts, etc.) is gathered and stored in the hybrid data structure 112. In order to determine a prediction score, the selection engine 110 is configured to access the hybrid data structure 112 and to retrieve data related to each of the hybrids in the pool of hybrids, such as, for example, the hybrid designated $F_1+M_1$, $F_1+M_2$, $F_1+M_m$, $F_2+M_1$, $F_3+M_1$, $F_4+M_1$, up to $F_n+M_m$ in Table 2. As shown, the phenotypic data from the hybrid data structure 112 is included in the Table 2 for each of the hybrids. The selection engine 110 is configured to then generate a prediction score based on the retrieve data and the prediction model and, from the data, determine a prediction score for each hybrid.

TABLE 2

| Hybrid | Yield | Height | Stand | Selection |
|---|---|---|---|---|
| $F_1 + M_1$ | $Y_{1,1}$ | $H_{1,1}$ | $S_{1,1}$ | TRUE |
| $F_1 + M_2$ | $Y_{1,2}$ | $H_{1,2}$ | $S_{1,2}$ | FALSE |
| ... | ... | ... | ... | ... |
| $F_1 + M_m$ | $Y_{1,m}$ | $H_{1,m}$ | $S_{1,m}$ | FALSE |
| $F_2 + M_1$ | $Y_{2,1}$ | $H_{2,1}$ | $S_{2,1}$ | TRUE |
| $F_3 + M_1$ | $Y_{3,1}$ | $H_{3,1}$ | $S_{3,1}$ | TRUE |
| $F_4 + M_1$ | $Y_{4,1}$ | $H_{4,1}$ | $S_{4,1}$ | TRUE |
| ... | ... | ... | ... | ... |
| $F_n + M_m$ | $Y_{n,m}$ | $H_{n,m}$ | $S_{n,m}$ | FALSE |

In addition, the selection engine 110 is configured to select a group of hybrids from the pool of hybrids based on the prediction score. Specifically, the selection engine 110 may be configured to select hybrids with prediction scores that satisfy one or more thresholds, or, alternatively, order the hybrids, based on the prediction scores, and then select a number of hybrids based on the index. In Table 2, for example, the group of hybrids selected, by the selection engine 110, includes the hybrids designated "TRUE," but not the hybrids designated "FALSE."

The selection engine 110 is further configured to then identify a set of hybrids, from the group of hybrids, to advance to a next iteration of the cultivation and testing phase 106 and/or to the validation phase 108. To do so, the selection engine 110 is configured to employ one or more algorithms, as described herein or otherwise, to account for a performance of the hybrids (e.g., based on the prediction score, etc.), and also one or more other factors related to the hybrids. The factors may be related to, for example, line distribution (e.g., male and/or female, etc.), heterotic diversity (e.g., male and/or female, etc.), traits (e.g., disease resistance, etc.), market segmentation, risk, production costs, trait availability/readiness, etc., as described herein. When suitable, the selection engine 110 may be configured to perform further iterations of the cultivation and testing phase 106 and/or the algorithms herein, to identify the set of hybrids with a desired number of hybrids included therein.

Finally, in the breeding pipeline 102, the selection engine 110 is configured to direct the identified set of hybrids to a further iteration of the cultivation and testing phase 106 and/or to the validation phase 108, in which the hybrids are exposed to pre-commercial testing or other suitable processes (e.g., a characterization and/or commercial development phase, etc.) with a goal and/or target of planting and/or commercialization of the hybrids. For example, one or more plant products (e.g., seeds, etc.) may be included in a growing space of the breeding pipeline 102 (e.g., the cultivation and testing phase 106, the validation phase 108, etc.), whereby the one or more plant products are derived from the identified set of hybrids (e.g., one or more plant products per identified hybrid, etc.). That is, the identified set of hybrids may then be subjected to one or more additional testing and/or selection methods, trait integration, and potentially, one or more bulking techniques to prepare the hybrids, or plant material based thereon, for further testing and/or commercial activities.

Figure 2:
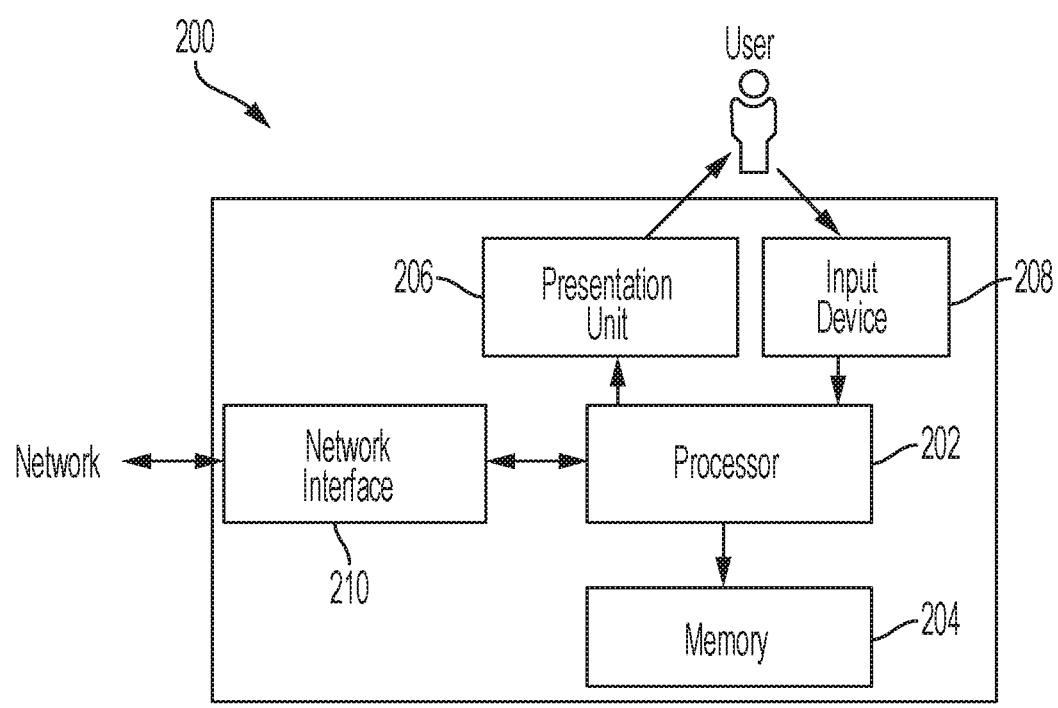
FIG. 2 is a block diagram of a computing device that may be used in the exemplary system of FIG. 1.

FIG. 2 illustrates an exemplary computing device 200 that may be used in the system 100, for example, in connection with various phases of the breeding pipeline 102, in connection with the selection engine 110, the hybrid data structure 112, etc. For example, at different parts of the breeding pipeline 102, breeders or other users interacting with computing devices, consistent with computing device 200, enter data and/or access data in the hybrid data structure 112 to support breeding decisions and/or testing completed/ accomplished by such breeders, or other users. Further, the selection engine 110 includes at least one computing device consistent with computing device 200. In connection therewith, the selection engine 110 of the system 100 includes at least one computing device consistent with computing device 200. The computing device 200 may be configured, by executable instructions, to implement the various algorithms and other operations described herein with regard to the selection engine 110. It should be appreciated that the system 100, as described herein, may include a variety of different computing devices, either consistent with computing device 200 or different from computing device 200.

The exemplary computing device 200 may include, for example, one or more servers, workstations, personal computers, laptops, tablets, smartphones, other suitable computing devices, combinations thereof, etc. In addition, the computing device 200 may include a single computing device, or it may include multiple computing devices located in close proximity or distributed over a geographic region, and coupled to one another via one or more networks. Such networks may include, without limitations, the Internet, an intranet, a private or public local area network (LAN), wide area network (WAN), mobile network, telecommunication networks, combinations thereof, or other suitable network(s), etc. In one example, the hybrid data structure 112 of the system 100 includes at least one server computing device, while the selection engine 110 includes at least one separate computing device, which is coupled to the hybrid data structure 112, directly and/or by one or more LANs, etc.

With that said, the illustrated computing device 200 includes a processor 202 and a memory 204 that is coupled to (and in communication with) the processor 202. The processor 202 may include, without limitation, one or more processing units (e.g., in a multi-core configuration, etc.), including a central processing unit (CPU), a microcontroller, a reduced instruction set computer (RISC) processor, an application specific integrated circuit (ASIC), a programmable logic device (PLD), a gate array, and/or any other circuit or processor capable of the functions described herein. The above listing is exemplary only, and thus is not intended to limit in any way the definition and/or meaning of processor.

The memory 204, as described herein, is one or more devices that enable information, such as executable instructions and/or other data, to be stored and retrieved. The memory 204 may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, tapes, hard disks, and/or any other type of volatile or nonvolatile physical or tangible computer-readable media. The memory 204 may be configured to store, without limitation, the hybrid data structure 112, phenotypic data, testing data, set selection algorithms, inbred lines, various thresholds, prediction models, and/or other types of data (and/or data structures) suitable for use as described herein, etc. In various embodiments, computer-executable instructions may be stored in the memory 204 for execution by the processor 202 to cause the processor 202 to perform one or more of the functions described herein, such that the memory 204 is a physical, tangible, and non-transitory computer-readable storage media. It should be appreciated that the memory 204 may include a variety of different memories, each implemented in one or more of the functions or processes described herein.

In the exemplary embodiment, the computing device 200 also includes a presentation unit 206 that is coupled to (and is in communication with) the processor 202. The presentation unit 206 outputs, or presents, to a user of the computing device 200 (e.g., a breeder, etc.) by, for example, displaying and/or otherwise outputting information such as, but not limited to, selected hybrids, progeny from hybrids as commercial products, and/or any other type of data. It should be further appreciated that, in some embodiments, the presentation unit 206 may comprise a display device such that various interfaces (e.g., applications (network-based or otherwise), etc.) may be displayed at computing device 200, and in particular at the display device, to display such information and data, etc. And in some examples, the computing device 200 may cause the interfaces to be displayed at a display device of another computing device, including, for example, a server hosting a website having multiple webpages, or interacting with a web application employed at the other computing device, etc. Presentation unit 206 may include, without limitation, a liquid crystal display (LCD), a light-emitting diode (LED) display, an organic LED (OLED) display, an "electronic ink" display, combinations thereof, etc. In some embodiments, presentation unit 206 includes multiple units.

The computing device 200 further includes an input device 208 that receives input from the user. The input device 208 is coupled to (and is in communication with) the processor 202 and may include, for example, a keyboard, a pointing device, a mouse, a stylus, a touch sensitive panel (e.g., a touch pad or a touch screen, etc.), another computing device, and/or an audio input device. Further, in some exemplary embodiments, a touch screen, such as that included in a tablet or similar device, performs as both presentation unit 206 and input device 208. In at least one exemplary embodiment, the presentation unit and input device are omitted.

In addition, the illustrated computing device 200 includes a network interface 210 coupled to (and in communication with) the processor 202 (and, in some embodiments, to the memory 204 as well). The network interface 210 may include, without limitation, a wired network adapter, a wireless network adapter, a telecommunications adapter, or other device capable of communicating to one or more different networks. In at least one embodiment, the network interface 210 is employed to receive inputs to the computing device 200. For example, the network interface 210 may be coupled to (and in communication with) in-field data collection devices, in order to collect data for use as described herein. In some exemplary embodiments, the computing device 200 may include the processor 202 and one or more network interfaces incorporated into or with the processor 202.

Figure 3:
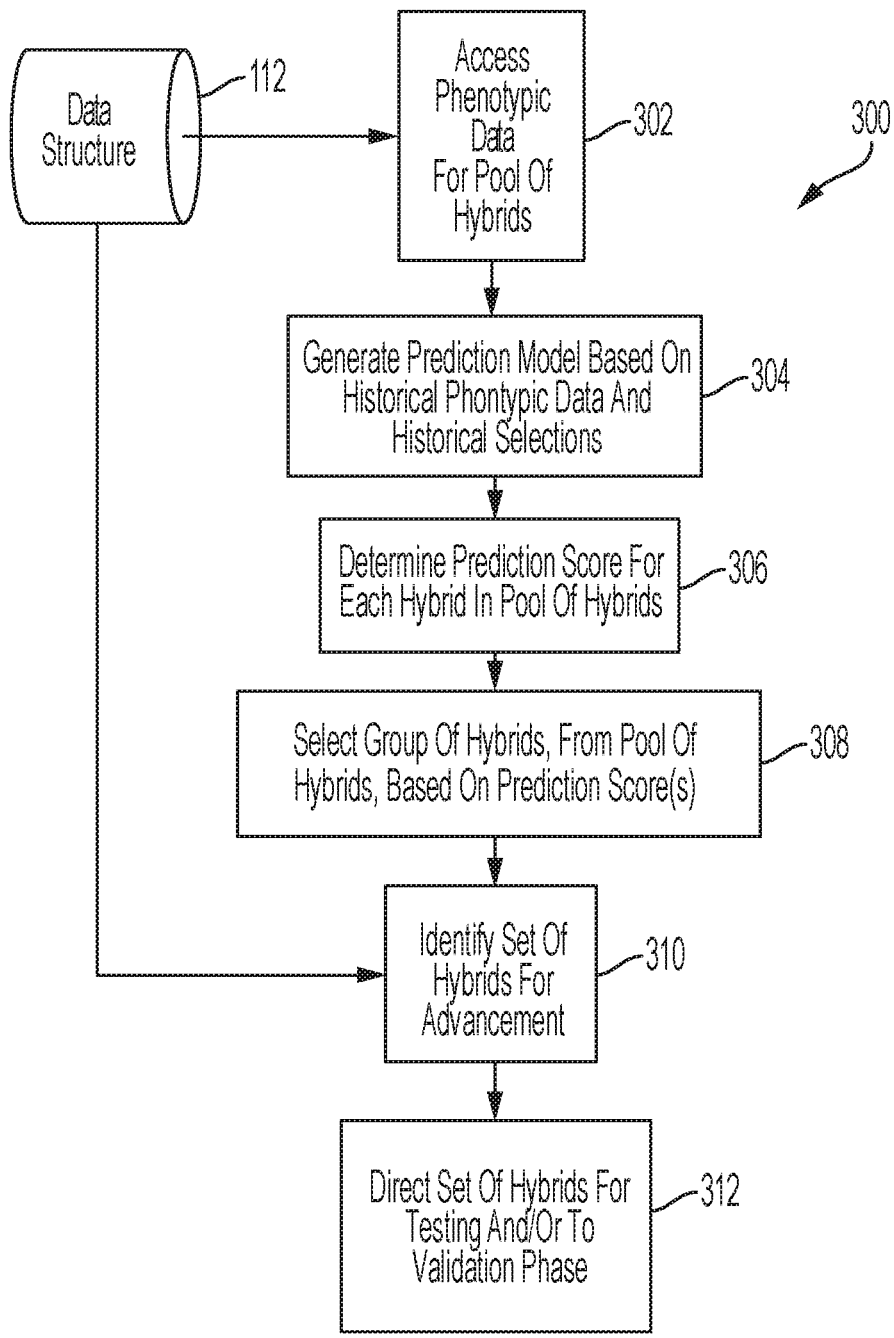
FIG. 3 is an exemplary method, suitable for use with the system of FIG. 1, for use in identifying a set of hybrids from a pool of potential hybrids.

FIG. 3 illustrates an exemplary method 300 for identifying a set of hybrids from a pool of potential hybrids to be advanced in a breeding pipeline. The exemplary method 300 is described herein in connection with the system 100, and may be implemented, in whole or in part, in the breeding pipeline 102, the selection engine 110 and the hybrid data structure 112 of the system 100. Further, for purposes of illustration, the exemplary method 300 is also described with reference to the computing device 200 of FIG. 2. However, it should be appreciated that the method 300, or other methods described herein, are not limited to the system 100 or the computing device 200. And, conversely, the systems, data structures, and the computing devices described herein are not limited to the exemplary method 300.

Figure 4:
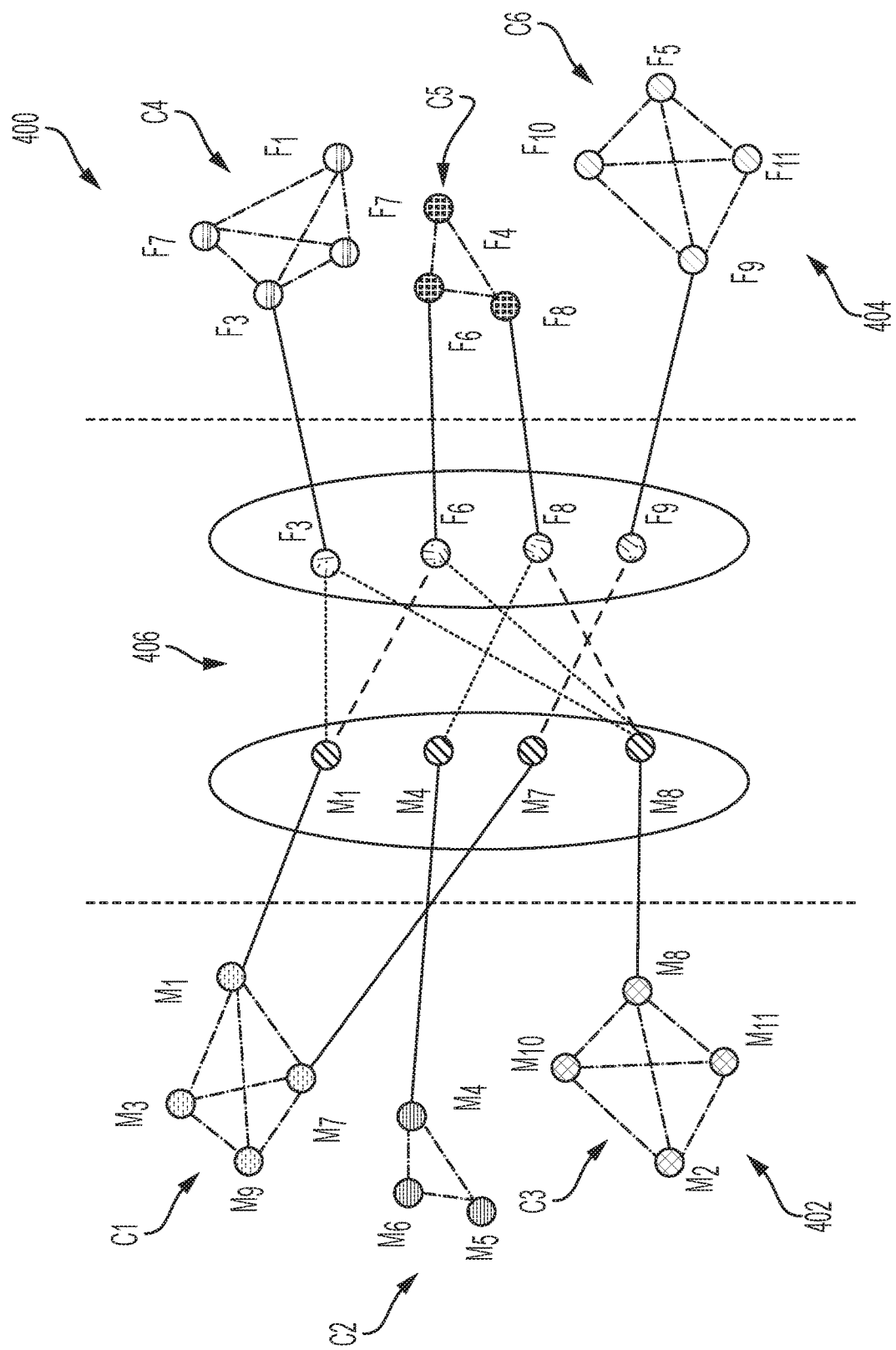
FIG. 4 includes a bipartite graphic representing identification of a set of hybrids from a plurality of lines, which form a pool of hybrids.

To begin, a breeder (or other user) initially selects a plant type (e.g., maize, etc.) for which a set of hybrids is to be identified. From this selection, a series of lines is identified for the plant type, where the lines are segregated into two heterotic pools: male lines and female lines. FIG. 4 illustrates a bipartite graphic 400, which includes the series of lines, each of which is illustrated as a node and designated $M_1$ through $M_{11}$ or $F_1$ through $F_{11}$. It should be appreciated that the number of lines included in FIG. 4 is for illustrative purposes only, and that a different number of lines (e.g., 100 lines per heterotic group (or more or less), etc.) will generally be included in one or more implementations of the method 300. As shown, in FIG. 4, the illustrated lines are segregated into the male heterotic pool 402 and the female heterotic pool 404. The male lines are then crossed with the female lines, as shown in FIG. 4, to provide hybrids, and more specifically, a pool of hybrids from which a set of hybrids is to be identified. The pool of hybrids includes, for example, hybrids designated $F_1+M_1$, $F_1+M_2$ ... $F_2+M_1$ ... $F_n+M_m$, which is inclusive of the hybrids 406 shown in FIG. 4 by the line connectors between the male lines and the female lines (e.g., hybrid $F_3+M_1$, etc.).

Notwithstanding the illustrated example of FIG. 4, where 100 male lines (n=100) and 100 female lines (m=100) are identified to the selection engine 110, the selection engine 110 may identify a set of 100 hybrids (r), for example, through use of the method 300.

As shown in FIG. 3, then, at the outset, the selection engine 110 accesses, at 302, phenotypic data for the hybrids within the hybrid data structure 112, where the phenotypic data includes, generally, both historical data related to past hybrids, and also current or present data related to the hybrids included in the pool of hybrids, i.e., $F_1+M_1$, $F_1+$ $M_2 \ldots F_2+M_1 \ldots F_n+M_m$. The historical data may include, without limitation, yield data, height data and stability data, for maize, for each of the lines included in prior hybrids, and also historical selections of the hybrids, where TRUE, for example, indicates the hybrid was advanced in a prior breeding program, and where FALSE, for example, indicates the hybrid was not advanced in the prior breeding program. In this exemplary embodiment, the selection engine 110 generates, at 304, a prediction model based on the historical phenotypic data for the past hybrids and the historical selections, where the model provides a prediction score (based on phenotypic data) that is indicative of the probability of the hybrid being selected. The prediction model may be generated, by the selection engine 110, through one or more different supervised, unsupervised, or semi-supervised algorithms/models, such as, but not limited to, random forest, support vector machine, logistic regression, tree based algorithms, naïve Bayes, linear/logistic regression, deep learning, nearest neighbor methods, Gaussian process regression, and/or various forms of recommendation systems algorithms, etc.

Once the prediction model is generated, the selection engine 110 generates, at 306, prediction scores for each of the hybrids in the pool of hybrids (e.g., $F_1+M_1 \ldots F_n+M_m$, etc.), based on phenotypic data for the hybrids (accessed in the hybrid data structure 112 in memory 204) and the prediction model.

Subsequently, the selection engine 110 selects a group of hybrids from the pool of hybrids, at 308, based on the prediction scores generated at 306. The selection, by the selection engine 110, may be accomplished in a variety of different manners utilizing the prediction scores. In this exemplary embodiment, for example, the selection engine 110 indexes the hybrids based on the associated prediction scores (e.g., in order from highest to lowest, etc.), from which the selection engine 110 then selects the group of hybrids as the top number (e.g., the top 6,000 hybrids, etc.) from the ordered pool of hybrids (at 308). In other examples, the selection engine 110 may apply one or more thresholds to the prediction scores to retain hybrids having prediction scores that satisfy the one or more thresholds (e.g., are greater (or less) than the threshold(s), etc.), while not selecting hybrids with prediction scores that fail to satisfy the one or more thresholds. From the group of hybrids in FIG. 4, for example, as indicated in Table 2, the hybrids $F_1+M_1$, $F_2+M_1$, $F_3+M_1$, and $F_n+M_1$ are selected to the group of hybrids, at 308, from the pool of hybrids, while the hybrids $F_1+M_2$, $F_1+M_m$, and $F_n+M_m$ are not.

Next in the method 300, the selection engine 110 identifies, at 310, a set of hybrids from the group of hybrids, based on one or more set identification algorithms. In general, the set identification algorithm(s) is based on a probability of success of the hybrids, which is and/or is derived from the prediction score for each hybrid in the group of hybrids (e.g., as determined at 306, etc.). In addition, the selection engine 110 also relies on one or more factors to refine and/or alter the set of hybrids which may be identified based on the predictions score alone. For example, the selection engine 110 may impose a trait limitation on the set of hybrids to be identified, or define desired line distribution or heterotic diversity profiles from which the identified set of hybrids defines a deviation or error, etc., which then counts as a penalty or cost, for example, to the probability of success of the hybrids in identifying the set of hybrids. Other factors may include, for example, risk, production cost (e.g., cost of goods, etc.), disease resistance or other traits (individual or combined), market segmentation, trait integration, trait availability or readiness, or other factors associated with the performance of the hybrids from a growth, effectiveness, and/or commercial success perspective, etc.

In this exemplary embodiment, the selection engine 110 employs the set identification algorithm as a series of algorithms which define a system to be solved. Specifically, two quadratic equations, one each for the male hybrids (Equation 1) and the female hybrids (Equation 3), are provided. Each is solved to provide a distribution of the lines, which are followed (i.e., as continuous variables) to the final identification of the set of hybrids. With that said, in terms of the bipartite graph of FIG. 4, the quadratic equations are associated with the heterotic pools 402 and 404. The mixed integer programming selects edges of the bipartite graph, which follows a desired node profile distinction, specific to one or more optimizers. By use of the mixed integer programming, several populations distributions in the set of hybrids identified at 310 is also maintained. The optimizers $y_*^f$ and $y_*^m$ included in the equations (Equations 1-4 below) are used as the input to the mixed integer program then used in a mixed integer program to identify the set of hybrids. The female quadratic equation (Equation 1) is as follows:

$$\text{maximize } \lambda_p(b_i^f)^T y_*^f - \lambda_d (y_*^f)^T S_f y_*^f \qquad (1)$$

In connection therewith, Equation 1 is subject to Equation 2:

$$1^T y_*^f = 1, 0 \leq y_*^f \leq 1 \qquad (2)$$

The male quadratic equation (Equation 3) is as follows:

$$\text{maximize } \lambda_p(b_i^m)^T y_*^m - \lambda_d (y_*^m)^T S_m y_*^m \qquad (3)$$

In connection therewith, Equation 3 is subject to Equation 4:

$$1^T y_*^m = 1, 0 \leq y_*^m \leq 1 \qquad (4)$$

In the female quadratic equation (and similarly for the male quadratic equation), $(b_i^f)^T y_*^f$, and $(y_*^f)^T S_f y_*^f$ denote linear performance and the quadratic diversity of the line usage, where $b_i^f$ is the probability of success of the female line (e.g., by averaging probability for the associated hybrids, or by determining and/or retrieve probability specific to the female lines, etc.). The female lines with 100% homology will have a value of "1." Female lines with 0% homology will have a value of "0." Most lines will share some homology, and are scored as a decimal between 0 and 1. An exemplary pairwise matrix for the lines in the female heterotic pool or $S_f$ is provided below in Table 3.

TABLE 3

|       | $F_1$ | $F_2$ | $F_3$ | $F_4$ | ... | $F_n$ |
|-------|-------|-------|-------|-------|-----|-------|
| $F_1$ | 1     | 0.65  | 0.65  | 0.89  | ... | ...   |
| $F_2$ | 0.65  | 1     | 0.78  | 0.60  | ... | ...   |
| $F_3$ | 0.65  | 0.78  | 1     | 0.87  | ... | ...   |
| $F_4$ | 0.89  | 0.60  | 0.87  | 1     | ... | ...   |
| ...   | ...   | ...   | ...   | ...   | 1   | ...   |
| $F_n$ | ...   | ...   | ...   | ...   | ... | 1     |

In addition, $(b_i^m)^T y_*^m$ and $(y_*^m)^T S_m y_*^m$ denote linear performance and the quadratic diversity of the line usage, where $b_i^m$ is the probability of success of the male line (e.g., by averaging probability for the associated hybrids, or by determining and/or retrieve probability specific to the female lines, etc.). Again, male lines with 100% homology will have a value of "1." Male lines with 0% homology will have a value of "0." Most lines will share some homology, and are scored as a decimal between 0 and 1. An exemplary pairwise matrix for the lines in the male heterotic pool or $S_m$ is provided below in Table 4 (and based on the clustering of the lines, as described below).

TABLE 4

|     | $M_1$ | $M_2$ | $M_3$ | $M_4$ | ... | $M_m$ |
| --- | --- | --- | --- | --- | --- | --- |
| $M_1$ | 1 | 0.75 | 0.98 | 0.89 | ... | ... |
| $M_2$ | 0.75 | 1 | 0.77 | 0.84 | ... | ... |
| $M_3$ | 0.98 | 0.77 | 1 | 0.81 | ... | ... |
| $M_4$ | 0.89 | 0.84 | 0.81 | 1 | ... | ... |
| ... | ... | ... | ... | ... | 1 | ... |
| $M_m$ | ... | ... | ... | ... | ... | 1 |

Genetic diversity is included in the set identification algorithm to limit and/or mitigate risk associated with usage of lines with similar genetic backgrounds with high intensity within the identified set of hybrids. Once these distributions of line usages are identified, the optimizers $y_*^f$ and $y_*^m$ are employed, by the selection engine 110, to identify, subject to the below, a set of hybrids, which follow the desired and/or required line usage with given and/or desired probability of success (e.g., a relative high, or the highest, probability of success).

In connection with the above, the selection engine 110 employs the following mixed integer algorithm to identify a set of hybrids, $x_{OPT}$, from the group of hybrids, at 310. This exemplary algorithm below (Equation 5), in combination with, or in connection with, the quadratic equations above (Equations 1-4), is also referred to herein as the set identification algorithm.

$$x_{OPT} = \arg\max \lambda_p \Sigma_{i=1}^N x_i p_i - \lambda_{d_m} 1^T \theta_m - \lambda_{d_f} 1^T \theta_f - \lambda_{h_m} 1^T \gamma_m - \lambda_{h_f} 1^T \gamma_f \quad (5)$$

In connection therewith, Equation 5 is subject to Equations 6-11:

$$\Sigma_{i=1}^N x_i = r; x_i \in \{0,1\}^N \quad (6)$$

$$-\theta_m(i) \leq \Sigma_{j=1}^N M_m(i,j) * x_j - y_i^m \leq \theta_m(i) \quad (7)$$

$$-\theta_f(i) \leq \Sigma_{j=1}^N M_f(i,j) * x_j - y_i^f \leq \theta_f(i) \quad (8)$$

$$-\gamma_m(i) \leq \Sigma_{j=1}^N M_h^m(i,j) * x_j - h_i^m \leq \gamma_m(i) \quad (9)$$

$$-\gamma_f(i) \leq \Sigma_{j=1}^N M_h^f(i,j) * x_j - h_i^f \leq \gamma_f(i) \quad (10)$$

$$\alpha_{T_k}^l(i) \leq \Sigma_{j=1}^N M_{T_k}(i,j) * x_j \leq \alpha_{T_k}^h(i) \quad (11)$$

For the above, the selection engine 110 is provided to identify r hybrids to the set of hybrids, at 310, where r may include, for example, 100 hybrids.

The term $p_i$ is indicative of a probability of success, and is generated by the prediction algorithm for hybrids. Specifically, the term $p_i$ is computed as a combination of the prediction score (determined at 306) and one or more phenotype traits. The term $p_i$ then reflects a linear combination of dominant traits, where the weights are defined by mutual information associated with historical data. In this manner, a more discrete manner of evaluating the performance is provided for the group of hybrids, as compared to the broader pool of progenies described above.

In Equations 7 and 8, the profile to be followed by the set of hybrids is provided from the quadratic questions (e.g., Equations 1-5, etc.), as $y_*^f$ and $y_*^m$ above. In addition, the term $M_m$ is indicative of the incidence matrix from a set of hybrids for a set of male lines, where the presence of a particular male line is a "1" and the absence of a particular male line is "0". A simplified example matrix is illustrated below in Table 5.

TABLE 5

|     | $F_1 + M_1$ | $F_1 + M_2$ | $F_1 + M_3$ | $F_2 + M_1$ | $F_2 + M_2$ | $F_2 + M_3$ | $F_3 + M_1$ | ... |
| --- | --- | --- | --- | --- | --- | --- | --- | --- |
| $M_1$ | 1 | 0 | 0 | 1 | 0 | 0 | 0 | ... |
| $M_2$ | 0 | 1 | 0 | 0 | 1 | 0 | 0 | ... |
| $M_3$ | 0 | 0 | 1 | 0 | 0 | 1 | 0 | ... |
| ... | ... | ... | ... | ... | ... | ... | ... | ... |

The term $M_f$ is indicative of the incidence matrix from a set of hybrids for a set of female lines, where the presence of a particular female line is a "1" and the absence of a particular female line is "0". A simplified example matrix is illustrated below in Table 6.

TABLE 6

|     | $F_1 + M_1$ | $F_1 + M_2$ | $F_1 + M_3$ | $F_2 + M_1$ | $F_2 + M_2$ | $F_2 + M_3$ | $F_3 + M_1$ | ... |
| --- | --- | --- | --- | --- | --- | --- | --- | --- |
| $F_1$ | 1 | 1 | 1 | 0 | 0 | 0 | 0 | ... |
| $F_2$ | 0 | 0 | 0 | 1 | 1 | 1 | 0 | ... |
| $F_3$ | 0 | 0 | 0 | 0 | 0 | 0 | 1 | ... |
| ... | ... | ... | ... | ... | ... | ... | ... | ... |

Based on the above, the set identification algorithm, in Equation 5, will impose a penalty or cost, when the set of hybrids (x) deviates from the profiles for the male line distributions and the female line distributions, which may inculcate, for example, an over representation of certain lines from in the set of hybrids to be identified.

From the above, the Equations 7 and 8 provide deviations $\theta_m(i)$ and $\theta_f(i)$ from the profile defined by the quadratic equations above, which is a desired profile. The deviations, when included in Equation 5 (the set identification algorithm), then each provide a cost or penalty to the set of hybrids for the deviation from the desired profile. That is, a cost is assigned to the deviation from the desired profile for both male and female line distribution. While provided in a specific manner in this exemplary embodiment, line distribution for one or both of male lines and/or female lines (or even the hybrids, potentially) may be provided otherwise in different embodiments (or even omitted, as a factor, in still other embodiments).

Further, through Equations 9 and 10, the set identification algorithm (Equation 5) accounts for heterotic diversity for each of the male lines and the female lines included in the set of hybrids. As shown in FIG. 4, each of the lines in each of the heterotic pools 402 and 404 is grouped into one or more clusters. Specifically, for example, the selection engine 110, or other computing device associated with the method 300, may use the following distance metric (as represented by Equations 12 and 13) to classify the inbred lines into the heterotic pools.

$$l_{ij} := 1 - e^{-\frac{(1-s_{ij})^2}{a^2}}, i \neq j \quad (12)$$

$$l_{ii} := -\sum_{j, j \neq i} l_{ij} \quad (13)$$

Here, $s_{ij}$ is the similarity between $i^{th}$ and $j^{th}$ lines, and $l_{ij}$ is the $ij^{th}$ cross entry of the Laplacian matrix L. In this example, the selection engine 110 employs spectral clustering, followed by Eigen Analysis, to determine/estimate a number of clusters (i.e., three in each of the heterotic pools 402 and 404 in FIG. 4), and then K-Means approach to cluster the inbred lines within the heterotic pools. It should be understood, however, that a variety of other known clustering techniques may alternatively be used. In this exemplary embodiment, the clustering is performed separately for male and female sets of inbred lines to identify the genetic pools among the lines. The selection engine 110, in this example, utilizes the Eigen Analysis to estimate the number of clusters in an unsupervised manner.

Then, once a desired number of clusters are determined, a dimensionality reduction is performed, by the selection engine 110, by projecting the Laplacian matrix L onto the dominant Eigen modes, for example, via the equations provided below (Equations 14 and 15). In the first equation below (Equation 14), L is the Laplacian matrix, created from the similarity distance $s_{ij}$, and $\hat{L}$ is the normalized Laplacian that is normalized by a diagonal matrix D. Eigen analysis of $\hat{L}$ provides the number of clusters. In the second equation below (Equation 15), the normalized Laplacian matrix is decomposed using a singular value decomposition. The matrix, $\Sigma$, contains the Eigen values that capture the number of the clusters according to spectral clustering. The selection engine 110 then clusters the lines $F_1$ through $F_{11}$ and $M_1$ through $M_{11}$ (in their respective heterotic pools 402 and 404) using a K-Means algorithm. Because the K-Means algorithm is a stochastic or random clustering mechanism, in this example, the selection engine 110 may cluster the lines in multiple different realizations of the K-Means algorithm, selecting the maximum, or a relatively high, inter cluster distance, etc. Again, while spectral clustering is used herein, it should be appreciated that other clustering algorithms may be employed, by the selection engine 110 or other computing device, including, for example, Hierarchical Clustering, Bayesian Clustering, C-means Clustering, etc.

$$\hat{L} = D^{-\frac{1}{2}} L D^{-\frac{1}{2}} \quad (14)$$

$$\hat{L} = U \Sigma U^T \quad (15)$$

As shown in FIG. 4, each of the lines is included in one of the clusters of lines, and associated with a distance or similarity to the other lines within the clusters. It should be appreciated, also, that the same marker based similarity matrix, or similar matrix, which is provided, in this embodiment, to characterize the diversity in the quadratic equation above. The same similarity matrix may therefore form the term $s_{ij}$ in the clustering and used to classify the lines into heterotic pools.

In addition, the term $M_h^m$ is indicative of the incidence matrix from progenies to male heterotic groups, where the presence of the male line in a cluster is indicative by "1" and the absence of the male line from the cluster is "0". A simplified example matrix $M_h^m$ is illustrated below in Table 7, where the clusters in FIG. 4 are designated $C_1$, $C_2$ and $C_3$ for the male heterotic pool 402.

TABLE 7

|       | $C_1$ | $C_2$ | $C_3$ |
|-------|-------|-------|-------|
| $M_1$ | 1 | 0 | 0 |
| $M_2$ | 0 | 0 | 1 |
| $M_3$ | 1 | 0 | 0 |
| $M_4$ | 0 | 1 | 0 |
| ...   | ... | ... | ... |
| $M_m$ | ... | ... | ... |

In addition, the term $M_h^f$ is indicative of the incidence matrix from progenies to male heterotic groups, where the presence of the female line in a cluster is indicative by "1" and the absence of the female line from the cluster is "0". A simplified example matrix $M_h^f$ is illustrated below in Table 8, where the clusters in FIG. 4 are designated $C_1$, $C_2$ and $C_3$ for the male heterotic pool 402.

TABLE 8

|       | $C_4$ | $C_5$ | $C_6$ |
|-------|-------|-------|-------|
| $F_1$ | 1 | 0 | 0 |
| $F_2$ | 1 | 0 | 0 |
| $F_3$ | 0 | 0 | 1 |
| $F_4$ | 0 | 1 | 0 |
| ...   | ... | ... | ... |
| $F_N$ | ... | ... | ... |

Further, with reference to Equation 9, the term $h_i^m$ is indicative of an average of the probability scores for the hybrids for the male line coming from the i-th heterotic pool. The term $h_i^m$ may be obtained, for example, by multiplying the score vector by mapping matrix $M_h^m$. And, with reference to Equation 10, the term $h_i^f$ is indicative of an average of the probability scores for the hybrids for the female line coming from the i-th heterotic pool. The term $h_i^f$ may be obtained, for example, by multiplying the score vector by mapping matrix $M_h^f$.

From the above, the Equations 9 and 10 provide deviations $\gamma_m(i)$ and $\gamma_f(i)$ from a desired profile for heterotic diversity for the male lines and the female lines, respectively. The deviations, when included in Equation 5, then each provide a cost or penalty to the set of hybrids for the deviation from that desired profile for heterotic diversity. That is, a cost is assigned to the deviation from the desired profile for both male and female heterotic diversity. While provided in a specific manner in this exemplary embodiment, heterotic diversity, or more generally, genetic diversity, for one or both of male lines and/or female lines (or even the hybrids, potentially) may be provided otherwise in different embodiments (or even omitted, as a factor, in still other embodiments).

With reference, now, to Equation 11, the term $M_{T_k}$ is indicative of the incidence matrix from hybrid trait $T_k$, and therefore, includes a matrix, like the ones above, where the values in the matrix, for each hybrid, include a 1 or a 0, for example, indicative of the presence of the trait in the hybrid, or not. It should be appreciated that the matrix for the hybrid may be provided as other than 0 or 1 to provide a more accurate indication of not only the presence or absence of the trait, but a degree of the trait, for certain types of traits.

In this manner, the term $M_{T_k}$ can be used to control the trait portfolios by the market segment. For example, for five market segments, $MS_1$, $MS_2$, $MS_3$, $MS_4$ and $MS_5$, and for each of the hybrids, based on their yields, disease susceptibility, etc., the term $M_{T_k}$ may be employed to identify into which market segments the trait may be potentially provided and/or launched. The following matrix in Table 9 provides a simple exemplary matrix for the hybrids to market segment.

TABLE 9

|       | $F_1 +$ $M_1$ | $F_1 +$ $M_2$ | $F_1 +$ $M_3$ | $F_2 +$ $M_1$ | $F_2 +$ $M_2$ | $F_2 +$ $M_3$ | $F_3 +$ $M_1$ | ... |
|-------|---|---|---|---|---|---|---|-----|
| $MS_1$ | 1 | 0 | 1 | 1 | 0 | 0 | 1 | ... |
| $MS_2$ | 0 | 1 | 1 | 1 | 1 | 0 | 0 | ... |
| $MS_3$ | 0 | 1 | 0 | 0 | 1 | 1 | 0 | ... |
| $MS_4$ | 1 | 1 | 0 | 0 | 0 | 1 | 1 | ... |
| $MS_5$ | 1 | 0 | 1 | 0 | 0 | 1 | 0 | ... |
| ...   | ... | ... | ... | ... | ... | ... | ... | ... |

As shown, similar to the matrixes above, the matrix of Table 9 includes a "1" to indicate the hybrid can be a potential candidate for a market segment, and includes a "0" to indicate the hybrid is not a candidate for the market segment. One hybrid can be eligible for multiple market segments. In the above example, $M_1+F_1$ is indicated for the market segments $MS_1$, $MS_4$ and $MS_5$. When the matrix is multiplied with the decision vector $x_j$ in Equation 11, it produces a portfolio distribution of the hybrids in different market segments. Based on the requirement of the market segment, as defined by one or more breeding and/or commercial strategies, the selection engine 110 may then realize and/or understand the bounds $\alpha_{T_k}^l(i)$ and $\alpha_{T_k}^h(i)$, which are the lower and upper portfolio bounds for trait $T_k$. The values for the bounds may be selected, by a human breeder, for example, and based on one or more business constraints and/or considerations (e.g., a desired market segment participation, a desired trait profile, etc.), or otherwise. It should be appreciated that, in this exemplary embodiment, Equation 11 does not impose a penalty or cost for the suitability of the set of hybrids for the market segments, but is a strict constraint on the set identification algorithm, such that it must be satisfied. That is, the set of hybrids identified by Equation 5 must include a set of hybrids that satisfies the upper and lower bounds provided in Equation 11.

It should be appreciated, however, that the trait factor (e.g., the market segment factor, etc.), may be different in other method embodiments, such that the trait factor (like the line distribution and/or heterotic diversity) applies a cost and/or penalty to Equation 5 (or other suitable algorithm) rather than being a strict constraint. It should further be appreciated that the other factors described herein may be provided, in a set identification algorithm, as a strict constraint, as above with regard to the trait factor (whereby the algorithm is forced to satisfy the constraint).

Further, while the market segmentation factor is determined and/or considered in provide in a specific manner in this exemplary embodiment, it may be considered and/or provided otherwise in different embodiments (or even omitted, as a factor, in still other embodiments).

Moreover, as shown above, Equation 5 includes multiple different weighting factors, with one related to the probability of success $\Delta_p$, one related to the line distribution actor for male lines $\Delta_{d_m}$, one related to the line distribution actor for female lines $\Delta_{d_f}$, one related to the heterotic diversity actor for male lines $\Delta_{h_m}$, and one related to the heterotic diversity actor for female lines $\Delta_{h_f}$, etc. It should be appreciated that the weights are selected, by the human breeder, to set priorities among the different factors associated with the weights. Where, for example, the line distribution is more important, a weighting factor may be imposed to increase the cost and/or penalty of deviation from the desired profiles $y_*^f$ and $y_*^m$. What's more, the weights, or a portion of the weights, may be selected based on historical data associated with the lines and/or hybrids, etc. In addition, a weight may be determined for the trait portfolio distribution (see, Equation 11 above), whereby it would provide a penalty or cost for deviation of the trait portfolio distribution of the identified set of hybrids from a desired profile, whereby the trait profile distribution would not be a strict constraint.

Other than the specific factors above (e.g., performance factors, etc.), risk may be further included as a linear cost in one or more of the quadratic equations and/or the mixed integer problems (or potentially, as a strict constraint in certain embodiments). Risk could be modeled as the chances of failure of the inbred line(s) or the hybrid for a given set of hybrids. While characterizing the risk of the line, the selection engine 110 may account for standability, disease susceptibility, etc., for example, or other traits and/or performance indicators of the lines, etc. In addition, or alternatively, when characterizing risk of the hybrid, the selection engine 110 may model the hybrid risk by standability, disease susceptibility, and cost of goods, etc. It should be appreciated that risk may be modeled as a linear cost with a negative coefficient so that the desired identified set of hybrids (e.g., in the above quadric equations (e.g., Equations 1-4, etc.) and/or Equation 5 as modified to include risk, etc.) would, in turn, provide for a limitation and/or restriction of the risk associated with the identified set of hybrids (as compared to other potential sets of hybrids).

As indicated above, the specific factors of line distribution, heterotic diversity, and market segmentation are presented for purposes of illustration and are not intended to limited the different permutations of factors that may be includes in one or more set identification algorithms. As such, different permutations of the factors described herein, along with different weights (or no weights) may be employed in other set identification algorithm, which are then used by the selection engine 110, where the algorithm may rely on the probability of success of the hybrids, the lines making up the hybrids, or some other basis for inclusion of the hybrids in the set of hybrids to be identified, etc.

Plainly, it should be appreciated that other set selection algorithms may be employed in other method embodiments.

Nonetheless, in this exemplary embodiment, Equation 5 is solved, in connection with the other equations, by the selection engine 110 to provide a vector for $x_i$ that includes a "1" for inclusion of the hybrids in the set of hybrids and a "0" for exclusion of the hybrids from the set of hybrids, thereby identify the hybrids to the set of hybrids, at 310. In the example, above, the selection engine 110 determines $x_i \in \{0,1\}^N$ to be a vector having 100 hybrids associated with a "1" indicating inclusion. Further, as shown in FIG. 3, the selection engine 110 then directs, at 312, the set of hybrids to further iterations of the cultivation and testing phase 106 and/or to the validation phase 108, thereby advancing the set of hybrids toward commercial activities. In connection therewith, one or more hybrids from the set of hybrids is included and/or compiled into a seed and/or other plant product, as needed, and is further included in a growing space of the breeding pipeline 102 (e.g., one or more greenhouses, shade houses, nurseries, breeding plots, fields, etc.). (e.g., in the cultivation and testing phase 106 and/or to the validation phase 108, etc.).

In addition to the above, the data related to the selection of the hybrids to the set of hybrids, by the selection engine 110, and further data related to the performance of the set of hybrids is included in the data structure 112 for use in further and/or subsequent iterations of the methods described herein for identifying hybrids for use in plant breeding pipelines (e.g., in pipeline 102, etc.).

In view of the above, the systems and methods herein permit the identification of hybrids to be advanced in a breeding pipeline. Specifically, in a commercial breeding pipeline, the number of potential hybrids from the inbred lines is substantially reduced, as demonstrated above. In this manner, a role of the breeder's expectations, tendencies and/or assumptions in the process is reduced, resulting in a more efficient capture of the commercially viable hybrids from the universe of potential hybrids. Through the systems and methods disclosed herein, breeders can vastly improve the associated breeding pipelines to identify and potentially select those hybrids for advancement based on analysis of a universe of data related to the hybrids, where conventional breeding methods are limited in what could be considered and how. Furthermore, the systems and methods herein are not limited geographically, or otherwise, in any way. For example, if a crop can be grown in a given area, the selection engine 110 herein can be used to identify a set of hybrids for that specific market/environment by weighting the data corresponding to certain traits that affect crop performance and/or success in that environment. Such environment may be represented globally or regionally, or it may be as granular as a specific location within a field (such that the same field is identified to have different such environments). In this way, the systems and methods herein may be used to target the development of products specific to certain markets, geographies, soil types, etc., or with directives to, maximize profits, maximize customer satisfaction, minimize production costs, etc.

With that said, it should be appreciated that the functions described herein, in some embodiments, may be described in computer executable instructions stored on a computer readable media, and executable by one or more processors. The computer readable media is a non-transitory computer readable media. By way of example, and not limitation, such computer readable media can include RAM, ROM, EEPROM, CD-ROM or other optical disk storage, magnetic disk storage or other magnetic storage device, or any other medium that can be used to carry or store desired program code in the form of instructions or data structures and that can be accessed by a computer. Combinations of the above should also be included within the scope of computer-readable media.

It should also be appreciated that one or more aspects of the present disclosure transform a general-purpose computing device into a special-purpose computing device when configured to perform the functions, methods, and/or processes described herein.

As will be appreciated based on the foregoing specification, the above-described embodiments of the disclosure may be implemented using computer programming or engineering techniques including computer software, firmware, hardware or any combination or subset thereof, wherein the technical effect may be achieved by performing at least one of the following operations: (a) accessing a data structure including data representative of a pool of hybrids; (b) determining, by at least one computing device, a prediction score for at least a portion of the hybrids included in the pool of hybrids based on the data included in the data structure, the prediction score indicative of a probability of selection and/or a probability of success of the hybrid based on historical data; (c) selecting, by the at least one computing device, a group of hybrids from the pool of progenies based on the prediction score; (d) identifying, by the at least one computing device, a set of hybrids, from the group of hybrids, based on an expected performance of the set of hybrids and/or one or more factors associated with the hybrids and/or lines making up the hybrids; and (e) directing the set of hybrids to a further iteration in a phase of a breeding pipeline or to a different phase of the breeding pipeline.

Examples and embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. In addition, advantages and improvements that may be achieved with one or more exemplary embodiments disclosed herein may provide all or none of the above mentioned advantages and improvements and still fall within the scope of the present disclosure.

Specific values disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may also be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on," "engaged to," "connected to," "coupled to," "associated with," "in communication with," or "included with" another element or layer, it may be directly on, engaged, connected or coupled to, or associated or in communication or included with the other feature, or intervening features may be present. As used herein, the term "and/or" includes any and all combinations of one or more of the associated listed items.

Although the terms first, second, third, etc. may be used herein to describe various features, these features should not be limited by these terms. These terms may be only used to distinguish one feature from another. Terms such as "first," "second," and other numerical terms when used herein do not imply a sequence or order unless clearly indicated by the context. Thus, a first feature discussed herein could be termed a second feature without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for use in identifying hybrids for use in a plant breeding pipeline, the method comprising:
    accessing a data structure including data representative of a pool of hybrids, each hybrid in the pool of hybrids including one male line and one female line, wherein the male lines and the female lines of the hybrids in the pool of hybrids define a pool of male lines and a pool of female lines;
    determining, by at least one computing device, a prediction score for at least a portion of the hybrids included in the pool of hybrids based on the data included in the data structure, the prediction score indicative of a probability of selection and/or a probability of success of the hybrid based on historical data;
    selecting, by the at least one computing device, a group of hybrids from the pool of hybrids based on the prediction score;
    identifying, by the at least one computing device, a set of hybrids, from the group of hybrids, based on: an expected performance of the set of hybrids, a diversity of usage of the male and female lines in the set of hybrids, and one or more factors associated with the hybrids and/or the male and female lines; and
    directing the set of hybrids to a further iteration in a phase of the breeding pipeline or to a different phase of the breeding pipeline.

2. The method of claim 1, wherein the historical data includes historical phenotypic data related to a plurality of hybrids and/or to the male and female lines of the plurality of hybrids and historical selections for each hybrid in the plurality of hybrids; and
    further comprising generating, by the at least one computing device, a prediction model based on the historical phenotypic data and the historical selections, wherein the plurality of hybrids and/or the male and female lines of the plurality of hybrids are associated with plant material of a type consistent with a plant type of the pool of hybrids; and
    wherein determining the prediction score for the at least a portion of the hybrids included in the pool of hybrids includes determining the prediction score based on the prediction model.

3. The method of claim 1, wherein the one or more factors includes one or more of: line distribution for the pool of male lines, line distribution for the pool of female lines, trait(s) or trait profiles, market segmentation, risk, product cost, trait availability, or trait readiness.

4. The method of claim 1, wherein identifying the set of hybrids is based on:
    diversity of usage of the female lines, as maximization of:

$$\lambda_p (b_i^f)^T y_*^f - \lambda_d (y_*^f)^T S_f y_*^f,$$

where $b_i^f$ is a probability of success of the female line, and $S_f$ is a pairwise matrix of homology of the pool of female lines, subject to:

$$1^T y_*^f = 1,\ 0 \le y_*^f \le 1;\ \text{and}$$

diversity of usage of the male lines, as maximization of:

$$\lambda_p (b_i^m)^T y_*^m - \lambda_d (y_*^m)^T S_m y_*^m$$

where $b_i^m$ is a probability of success of the male line, and $S_f$ is a pairwise matrix of homology of the pool of male lines, subject to:

$$1^T y_*^m = 1, 0 \le y_*^m \le 1.$$

5. The method of claim 1, wherein the data includes phenotypic data representative of the pool of hybrids; and
    wherein selecting the group of hybrids includes selecting the group of hybrids when the prediction score of the selected hybrid satisfies one or more thresholds.

6. The method of claim 1, wherein directing the set of hybrids to a different phase of the breeding pipeline includes including a plant product in a growing space of the breeding pipeline, after the set of hybrids is identified, the plant product based on at least one hybrid in the identified set of hybrids.

* * * * *